(12) United States Patent
Oura et al.

(10) Patent No.: US 11,204,619 B2
(45) Date of Patent: Dec. 21, 2021

(54) PATIENT MONITOR

(71) Applicant: NIHON KOHDEN CORPORATION, Tokyo (JP)

(72) Inventors: Mitsuhiro Oura, Tokyo (JP); Sou Kumagai, Tokyo (JP); Wataru Matuzawa, Tokyo (JP); Nobuyuki Yasumaru, Tokyo (JP); Kazuya Nagase, Tokyo (JP); Hiroshi Torigai, Tokyo (JP); Naoki Fukushima, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 745 days.

(21) Appl. No.: 16/071,022

(22) PCT Filed: Dec. 27, 2016

(86) PCT No.: PCT/JP2016/005240
§ 371 (c)(1),
(2) Date: Jul. 18, 2018

(87) PCT Pub. No.: WO2017/125991
PCT Pub. Date: Jul. 27, 2017

(65) Prior Publication Data
US 2019/0029635 A1    Jan. 31, 2019

(30) Foreign Application Priority Data

Jan. 19, 2016 (JP) .............................. JP2016-008260

(51) Int. Cl.
*G06F 1/04* (2006.01)
*A61B 5/00* (2006.01)
(Continued)

(52) U.S. Cl.
CPC .............. *G06F 1/04* (2013.01); *A61B 5/7285* (2013.01); *H04L 7/0008* (2013.01); *A61B 5/02* (2013.01); *A61B 8/06* (2013.01); *A61B 8/58* (2013.01)

(58) Field of Classification Search
CPC ....... G16H 10/60; G08B 21/0211; G06F 1/04; A61B 5/7285; A61B 5/02; A61B 8/06; A61B 8/58; H04L 7/0008
See application file for complete search history.

(56) References Cited

U.S. PATENT DOCUMENTS

| 5,904,708 A | 5/1999 | Goedeke |
| 2007/0033589 A1 | 2/2007 | Nicholas et al. |

(Continued)

FOREIGN PATENT DOCUMENTS

| EP | 1 061 997 A1 | 12/2000 |
| EP | 2 689 720 A1 | 1/2014 |

(Continued)

OTHER PUBLICATIONS

Communication dated Oct. 23, 2019, from the Japanese Patent Office in counterpart application No. 2016-008260.

(Continued)

*Primary Examiner* — Sung S Ahn
(74) *Attorney, Agent, or Firm* — Sughrue Mion, PLLC

(57) ABSTRACT

A patient monitor that acquires a vital sign through a measurement sensor, and that is to be connected to an external measurement apparatus for measuring another vital sign, includes a master clock that is disposed in the patient monitor, and that manages common time information, a first operating system that manages first time information, and a second operating system that manages second time information, and that transmits and receives data to and from the external measurement apparatus. When a predetermined (Continued)

event occurs, the first operating system reads the common time information from the master clock, and updates the first time information. When the predetermined event occurs, the second operating system reads the common time information from the master clock, updates the second time information, and notifies the external measurement apparatus of the updated second time information or the common time information.

18 Claims, 4 Drawing Sheets

(51) Int. Cl.
*H04L 7/00* (2006.01)
*A61B 5/02* (2006.01)
*A61B 8/00* (2006.01)
*A61B 8/06* (2006.01)

(56) References Cited

U.S. PATENT DOCUMENTS

| | | | | |
|---|---|---|---|---|
| 2009/0131762 A1* | 5/2009 | Pelzek | ............... | G04C 13/02 |
| | | | | 600/301 |
| 2010/0234718 A1* | 9/2010 | Sampath | ............... | A61B 5/002 |
| | | | | 600/407 |
| 2011/0252266 A1 | 10/2011 | Costa | | |
| 2014/0031639 A1 | 1/2014 | Toyomura et al. | | |
| 2015/0306409 A1* | 10/2015 | Greiner | ............... | A61N 1/3925 |
| | | | | 607/7 |

FOREIGN PATENT DOCUMENTS

| | | | |
|---|---|---|---|
| JP | 11-7428 | A | 1/1999 |
| JP | 2000-235406 | A | 8/2000 |
| JP | 2002-330930 | A | 11/2002 |
| JP | 2003-265419 | A | 9/2003 |
| JP | 2008-178626 | A | 8/2008 |
| JP | 2014-23570 | A | 2/2014 |
| WO | 03/071951 | A1 | 9/2003 |
| WO | 2009/138902 | A1 | 11/2009 |

OTHER PUBLICATIONS

Search Report dated Apr. 13, 2017, issued by the International Searching Authority in International Application No. PCT/JP2016/005240 (PCT/ISA/210).

Written Opinion dated Apr. 13, 2017, issued by the International Searching Authority in International Application No. PCT/JP2016/005240 (PCT/ISA/237).

* cited by examiner

PATIENT MONITOR

TECHNICAL FIELD

The present invention relates to a patient monitor, and more particularly to a patient monitor in which a plurality of operating systems operate.

BACKGROUND ART

As information for knowing the condition of a subject, various vital signs (the blood pressure, the body temperature, the respiration, the pulse rate, the arterial oxygen saturation, and the like) are widely employed. Moreover, an ultrasonic inspection apparatus is used for knowing the condition of the chest, abdomen, or the like of the subject.

In recent days, techniques for simultaneously performing measurement of a vital sign and ultrasonic measurement have been proposed. For example, PTL 1 discloses a system in which an ultrasonic transducer can be connected to a patient monitor (FIG. 1 of PTL 1). The system can simultaneously process an ultrasonic image acquired by the ultrasonic transducer, and a vital parameter (vital sign) of the subject.

Recently, in order to enhance the operation reliability and the expandability of the measurement function, furthermore, a configuration where a plurality of operating systems are caused to operate on the same patient monitor has been disclosed (PTL 2). In the vital sign measurement apparatus disclosed in PTL 2, a first OS (embedded OS) which is used for measuring a vital sign, and a second OS (general-purpose OS) with high expandability are caused to operate.

CITATION LIST

Patent Literature

[PTL 1]
WO/2009/138902
[PTL 2]
JP-A-2014-023570

SUMMARY OF INVENTION

Technical Problem

As described above, the configuration is used where an external measurement apparatus (preferably, an ultrasonic measurement apparatus) is connected to a patient monitor, and a plurality of operating systems operate on the patient monitor. In the case where a patient monitor having the configuration (a plurality of operating systems, and connection to an external measurement apparatus) is used, sets of time information of the respective operating systems must be synchronized with time information of the external measurement apparatus.

For example, a case where an ultrasonic measurement apparatus is connected to a patient monitor on which a plurality of operating systems operate to refer the blood pressure waveform and the like, and the Doppler blood flow image will be considered. In this case, if the sets of time information of the operating systems in the patient monitor, and the time information of the operating system in the ultrasonic measurement apparatus are not synchronized with one another, it is difficult for the doctor or the like to correctly determine relationships between the blood flow, the blood pressure waveform, and the like. Such difficulty occurs not only in the case where an ultrasonic measurement apparatus is connected to a patient monitor, but also in a case where another apparatus (an electromyograph, an EIT (Electrical Impedance Tomography) measurement apparatus, an electromagnetic blood flow meter) or the like is connected to a patient monitor.

In the above-described PTLs 1 and 2, however, there is no suggestion or teaching of time synchronization of the operating systems in the patient monitor, and the operating system in the external measurement apparatus.

The invention has been conducted in view of the above-described circumstances. It is a main object of the invention to provide a patient monitor on which a plurality of operating systems operate, and in which, in a configuration where an external measurement apparatus is connected to the patient monitor, the operating systems can respectively handle time information without time difference.

Solution to Problem

According to an aspect of the invention, a patient monitor that acquires a vital sign of a subject through a measurement sensor, and that is to be connected to an external measurement apparatus for measuring another vital sign of the subject, includes a master clock that is disposed in the patient monitor, and that manages common time information that is time information common to hardware, a first operating system that manages first time information that is internal specific time information, and a second operating system that manages second time information that is internal specific time information, and that transmits and receives data to and from the external measurement apparatus, wherein, when a predetermined event occurs, the first operating system reads the common time information from the master clock, and updates the first time information by using the common time information, and when the predetermined event occurs, the second operating system reads the common time information from the master clock, updates the second time information by using the common time information, and notifies the external measurement apparatus of the updated second time information or the common time information.

When a predetermined event occurs, the operating systems (the first operating system, the second operating system, and the operating system in the external measurement apparatus) use the common time information which is counted by the master clock to update the sets of time information which are respectively managed by the operating systems. Since the time synchronization is performed by using the common time information of the master clock, there is no time difference among the operating systems. Therefore, the patient monitor can handle a plurality of sets of information (a waveform, a measurement value, and an ultrasonic image) in a state where there is no time difference.

Advantageous Effects of Invention

It is possible to provide a patient monitor on which a plurality of operating systems operate, and in which, in a configuration where an external measurement apparatus is connected to the patient monitor, the operating systems can respectively handle sets of time information having no time difference.

DESCRIPTION OF EMBODIMENTS

Embodiment 1

Figure 1:
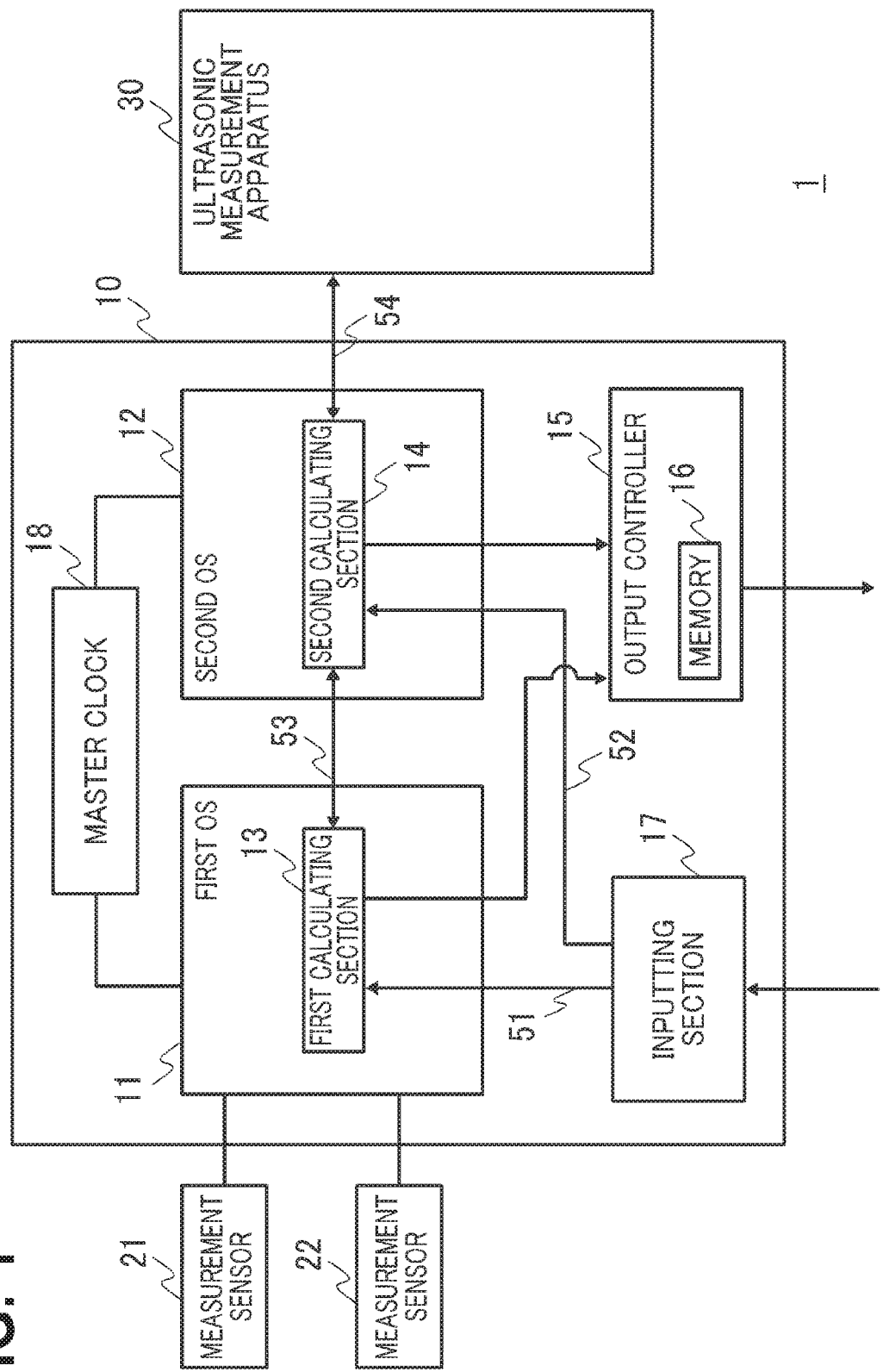
FIG. 1 is a block diagram illustrating the configuration of a patient monitor system 1 of Embodiment 1.

Hereinafter, an embodiment of the invention will be described with reference to the drawings. FIG. 1 is a block diagram illustrating the configuration of a patent monitor system 1 of the embodiment. The patient monitor system 1 has a patient monitor 10 and an ultrasonic measurement apparatus 30. The ultrasonic measurement apparatus 30 is a mode of the external measurement apparatus which is connected to the patient monitor 10, and which measures a vital sign (for example, an ultrasonic image) of a subject.

The patient monitor 10 is an apparatus which is to be disposed for each subject, and which measures, calculates, and displays a vital sign (the blood pressure, the oxygen saturation, the body temperature, the respiration, an electrocardiogram, an electromyogram, or the like). The patient monitor 10 is connected to measurement sensors 21, 22 which acquire various vital sign signals from the subject. Namely, the patient monitor 10 acquires a vital sign of the subject through the measurement sensors 21, 22. For example, the measurement sensors 21, 22 are an adhesive electrode, a cuff, a mask, a body temperature sensor, or the like. The measurement sensors 21, 22 are connected to the patient monitor 10 in a wired or wireless manner. The number of the measurement sensors may be arbitrarily set.

The patient monitor 10 may include a first OS 11 (Operating System, the first operating system), a second OS 12 (Operating System, the second operating system), an output controller 15, and an inputting section 17.

The first OS 11 performs basic control and management of a computer. A first calculating section 13 operates on the first OS 11. The first OS 11 is a basic software which provides a function of controlling programs, that of displaying a screen, that of operating files, and the like. The first OS 11 is a basic software which operates when a CPU (Central Processing Unit) that is not shown reads the OS from a memory, and then executes the OS.

The first OS 11 is an embedded type OS which can execute a specific function. For example, the specific function detects measurement waveforms and measurement values from the vital sign signals of the subject, and causes them to be displayed. An embedded type OS (hereinafter, also referred to as an embedded OS) is an OS which executes a preset specific function. As compared with a general-purpose OS (such as Windows, Mac OS, or Linux (all are registered trademarks)), therefore, an embedded OS has less possibility of stopping (freezing) a processing operation, and can realize a stable and highly reliable processing operation. The embedded OS, i.e., the first OS 11 is an OS which is employed in a bedside monitor that is disposed in the vicinity of the bed of the subject. Therefore, the first OS 11 is referred to also as the monitor OS.

Similarly with the first OS 11, the second OS 12 is a basic software which provides a function of controlling programs, that of displaying a screen, that of operating files, and the like. The second OS 12 is a basic software which operates when the CPU (Central Processing Unit) that is not shown reads the OS from a memory, and then executes the OS. As the second OS 12, a general-purpose OS (such as Windows, Mac OS, or Linux (all are registered trademarks)) which is used also in a personal computer (PC) is employed. A general-purpose OS has high expandability in utilize of a new application software, in management of a new peripheral device, in an application of a multilingual operation, and the like. The general-purpose OS, i.e., the second OS 12, is an OS having high expandability. In the following description, the second OS 12 is referred to as the extended OS.

The first calculating section 13 operates on the first OS 11. The first calculating section 13 processes a vital sign based on a control signal which is transmitted from the inputting section 17. The control signal is a signal which is based on contents that are input by the medical person through buttons or the like disposed on the housing of the patient monitor 10. The first calculating section 13 and the inputting section 17 are communicably connected to each other through a bus line 51. The measurement sensors 21, 22 for measuring a vital sign of the subject are connected to the first calculating section 13. The vital sign (vital sign signals) supplied from the measurement sensors 21, 22 are supplied to the first calculating section 13. Based on the control signal from the inputting section 17, the first calculating section 13 processes the vital sign signals.

The first calculating section 13 measures various numerical data (the blood pressure, the body temperature, the oxygen concentration, the carbon dioxide concentration, the cardiac output, and the like) related to the vital sign signals received from the measurement sensors 21, 22. Moreover, the first calculating section 13 produces lists and graphs of the measurement values based on the measured numerical data. The first calculating section 13 determines whether each of the measurement values indicates an abnormal value (a value which exceeds a preset threshold) or not, and, if it is determined that the measurement value indicates an abnormal value, produces an alarm display or the like. Then, the first calculating section 13 outputs the signals such as the biological waveform, the numerical data, the lists and graphs of the measurement values, and an abnormal alarm display, as calculation process signals (the first calculation signal) to the output controller 15. The first calculating section 13 stores the calculation process signals (the first calculation signal), the data received from the measurement sensors 21, 22, the inputting section 17, and a second calculating section 14, and the like, in storage means (a memory) which is not illustrated.

It is often that signals of vital signs measured by the measurement sensors 21, 22 are of the kind in which the vital signs are always and continuously measured from the subject by a bedside monitor. When the first calculating section 13 which processes the vital sign signals is caused to operate on the monitor OS (first OS 11) having high process reliability, therefore, it is possible to continuously obtain stable outputs of vital signs.

The second calculating section 14 operates on the second OS 12. The second calculating section 14 processes the vital signs based on a control signal which is transmitted from the inputting section 17. The second calculating section 14 and the inputting section 17 are communicably connected to each other through a bus line 52. The second calculating section 14 is communicably connected to the first calculating section 13 through a bus line 53.

Since the second calculating section 14 operates on the extended OS (second OS 12) having high expandability and versatility, the second calculating section 14 analyzes the calculation process signals transmitted from the first calculating section 13, and, by using the advanced function which cannot be processed by the embedded OS (first OS 11), can perform sophisticated graphic processes and the like such as a display of a vital sign analysis graph, a statistical process of data, a multilingual operation, and screen decoration.

The second calculating section 14 (second OS 12) is connected to the ultrasonic measurement apparatus 30 through a physical cable 54 (for example, a USB cable) to transmit and receive data to and from the ultrasonic measurement apparatus 30. The second calculating section 14 receives an ultrasonic image signal from the ultrasonic measurement apparatus 30, and processes the image signal, thereby causing an ultrasonic image to be displayed on a displaying section (for example, a display device disposed on the housing of the patient monitor 10 which is not illustrated) which is not illustrated, through the output controller 15.

The output controller 15 is configured by a graphic chip (video chip) which is an integrated circuit for performing image processing. The output controller 15 can simultaneously receive a plurality of signals, and performs a display control based on various calculation signals supplied from the first calculating section 13 and the second calculating section 14. Based on the received calculation signals, specifically, the output controller 15 causes various data, graphs, and the like to be displayed on the displaying section (for example, a display device disposed on the housing of the patient monitor 10) which is not illustrated. The output controller 15 further causes the ultrasonic image which is based on the ultrasonic image signal received from the ultrasonic measurement apparatus 30, to be displayed on the displaying section. In the display control, the output controller 15 adequately writes and reads data in and from a memory 16.

The inputting section 17 receives an input from various input interfaces (such as the buttons, knobs, touch panel, and the like on the housing of the patient monitor 10) which are not illustrated, and supplies a control signal corresponding to the input to the first calculating section 13 or the second calculating section 14.

A master clock 18 is an internal clock which, even when the patient monitor 10 is powered off, measures the present time. The master clock 18 manages (measures) time information (common time information) which is common to the hardware of the patient monitor 10. For example, the master clock 18 operates by receiving a power supply from a battery (such as a button cell or the like which is incorporated in the patient monitor 10) that is different from the power supply of the patient monitor 10.

The first OS 11 manages (measures) first time information which is internally unique time information. The first time information is a so-called system clock. When the patient monitor 10 is activated (the power supply is turned on), the first OS 11 reads the common time information from the master clock 18, and updates the first time information by using the read-out common time information. Here, the term "update" has a concept which includes "process of overwriting the first time information with the common time information," and "process of calculating the difference between the first time information and the common time information, and shifting the time indicated by the first time information, by using the difference." Namely, the term "update" has a concept which includes all processes of matching the first time information with the common time information. The above is applicable also in the following description.

Similarly, the second OS 12 manages (measures) second time information which is internally unique time information. The second time information is the so-called system clock. When the patient monitor 10 is activated (the power supply is turned on), the second OS 12 reads the common time information from the master clock 18, and updates the second time information by using the read-out common time information.

When a predetermined event occurs, moreover, the first OS 11 reads the common time information from the master clock 18, and updates the first time information by using the read-out common time information. When the predetermined event occurs, similarly, the second OS 12 reads the common time information from the master clock 18, and updates the second time information by using the read-out common time information. For example, the predetermined event is as follows:

a case where it is detected that the ultrasonic measurement apparatus 30 is physically connected to the patient monitor 10;

a case where a predetermined time period (for example, 30 minutes) has elapsed from the previous time synchronizing process;

a case where a notification notifying the start of the time synchronization with the master clock 18 is received from another operating system;

a case where software related to an ultrasonic image is activated or terminated in the second OS 12;

a case where the ultrasonic measurement apparatus 30 starts an ultrasonic measurement (a start signal is received);

a case where the ultrasonic measurement apparatus 30 ends the ultrasonic measurement (the start signal is terminated); and a case where the user explicitly inputs a time synchronization command (for example, a case where a dedicated synchronization button or the like is pressed).

The second OS 12 updates the second time information by using the common time information of the master clock 18, and notifies the ultrasonic measurement apparatus 30 of the updated second time information. Before the process of updating the second time information, the second OS 12 may notify the ultrasonic measurement apparatus 30 of the common time information. Namely, the second OS 12 notifies the ultrasonic measurement apparatus 30 of the read-out common time information or the updated second time information. The ultrasonic measurement apparatus 30 updates the system clock which is managed by the operating system in the ultrasonic measurement apparatus 30, by using the informed second time information (or the common time information).

The first OS 11 and the second OS 12 independently access the master clock 18, and therefore their read timings are preferably matched with each other. Before the first OS 11 reads the common time information from the master clock 18, for example, the reading is preferably notified to the second OS 12. In response to the notification, the second OS 12 accesses the master clock 18. In the case where the detection timings of a predetermined event in the operating systems are substantially identical to each other, the above-described timing matching is not necessary.

When a predetermined event occurs, the first OS 11, the second OS 12, and the ultrasonic measurement apparatus 30 correct in unison the respective sets of time information by using the common time information which is managed by the master clock 18. In order to correctly perform the time synchronization, preferably, the first OS 11 performs the above-described updating process (reading from the master clock 18 and updating of the first time information) in preference to other processes. Similarly, the second OS 12 preferably performs the above-described updating process (reading from the master clock 18, updating of the second time information, and notification of the second time information or the common time information) in preference to other processes. Namely, it is preferable that the updating process is handled as a high-priority interrupt process (a process which is immediately performed by temporarily halting a currently active process, or in other word a process which is performed in preference to other processes).

Each time when a predetermined event occurs, therefore, the sets of time information which are managed respectively in the operating systems (the first OS 11, the second OS 12, and the operating system in the ultrasonic measurement apparatus 30) are synchronized with one another by using the common time information.

Figure 2:
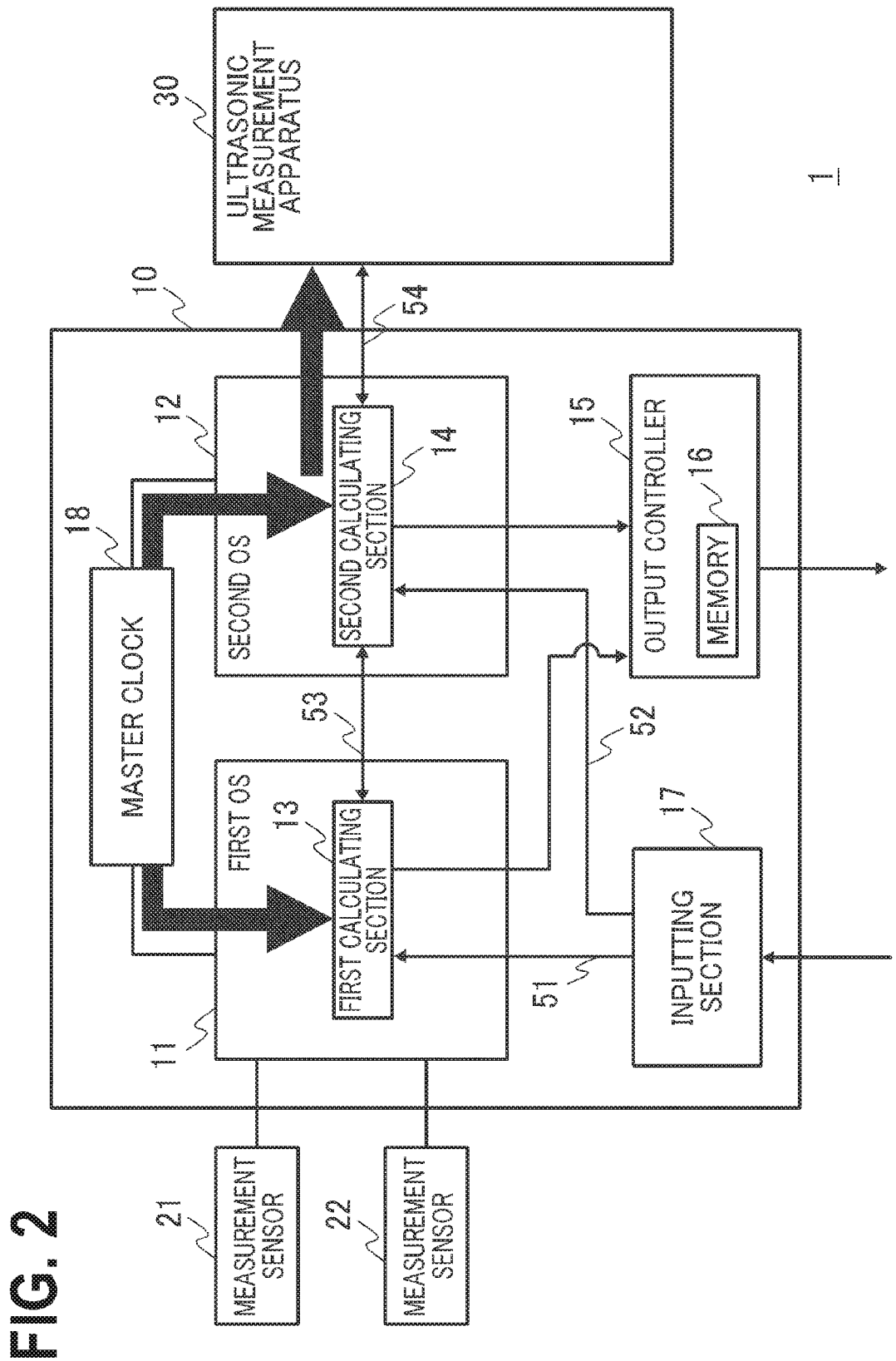
FIG. 2 is a block diagram illustrating the configuration of the patient monitor system 1 of Embodiment 1.

Then, the flow of the time synchronization in the case where a predetermined event occurs will be again described with reference to FIG. 2. When a predetermined event is detected, the first OS 11 and the second OS 12 read the common time information of the master clock 18, and update respectively the sets of time information (the first time information and the second time information) which are managed by the respective OSs (in other words, which are internally unique). Moreover, the second OS 12 notifies the ultrasonic measurement apparatus 30 of the updated second time information (or the common time information). The ultrasonic measurement apparatus 30 updates the time information which is managed by the operating system of the apparatus itself, by using the informed second time information (or the common time information).

In the case where an event which can be detected by only one of the operating systems in the patient monitor 10 occurs, the operating system which detects the event performs notification at first through the bus line 53. Then, the first OS 11 and the second OS 12 perform the above-described access to the master clock 18, and the like.

Then, the effect of the patient monitor 10 of the embodiment will be described. For example, a case where the ultrasonic measurement apparatus 30 acquires a blood flow image by means of Doppler measurement, and the patient monitor 10 simultaneously displays a blood pressure waveform and the like and the blood flow image will be considered. In this case, when the sets of time information of the operating systems are shifted from one another even if only slightly, there arise differences between information of peaks of the blood pressure and the like, and changes of the blood flow, and therefore it is difficult to correctly know the condition of the subject.

In the embodiment, when a predetermined event occurs, as described above, the operating systems (the first OS 11, the second OS 12, and the operating system in the ultrasonic measurement apparatus 30) cause the sets of time information which are managed respectively by the operating systems, to be synchronized with one another, by using the common time information which is counted by the master clock 18. The time synchronizations in which the common time information of the master clock 18 is used are performed at substantially same timings, and therefore there is no difference among the times in the operating systems. Consequently, the patient monitor 10 can handle a plurality of sets of information (a waveform, a measurement value, and an ultrasonic image) in a state where there is no time difference.

In the case where the ultrasonic measurement apparatus 30 and the patient monitor 10 are connected to each other in a wired manner, particularly, the second time information can be transmitted at high speed and stably. Moreover, the first OS 11 and the second OS 12 refer the master clock 18 in the same hardware without using a network. Namely, the exchange of time information among the operating systems (the first OS 11, the second OS 12, and the operating system in the ultrasonic measurement apparatus 30) can be performed at high speed and stably. As compared with the case where synchronization (for example, synchronization with an NTP (Network Time Protocol) server) is performed with using a network, therefore, an adverse influence such as a network delay can be avoided, and a state where there is little time difference among the three operating systems can be set.

In the operating systems, as described above, the process related to the time synchronization is preferentially performed (the process is executed as a high-priority interrupt process). When the time synchronization is performed with the highest priority, it is possible to set a state where the sets of time information which are managed respectively by the operating systems are more synchronized with one another.

Embodiment 2

Then, a patient monitor system 1 of the embodiment 2 will be described. Hereinafter, the patient monitor system 1 of the embodiment 2 will be described in points different from Embodiment 1.

Figure 3:
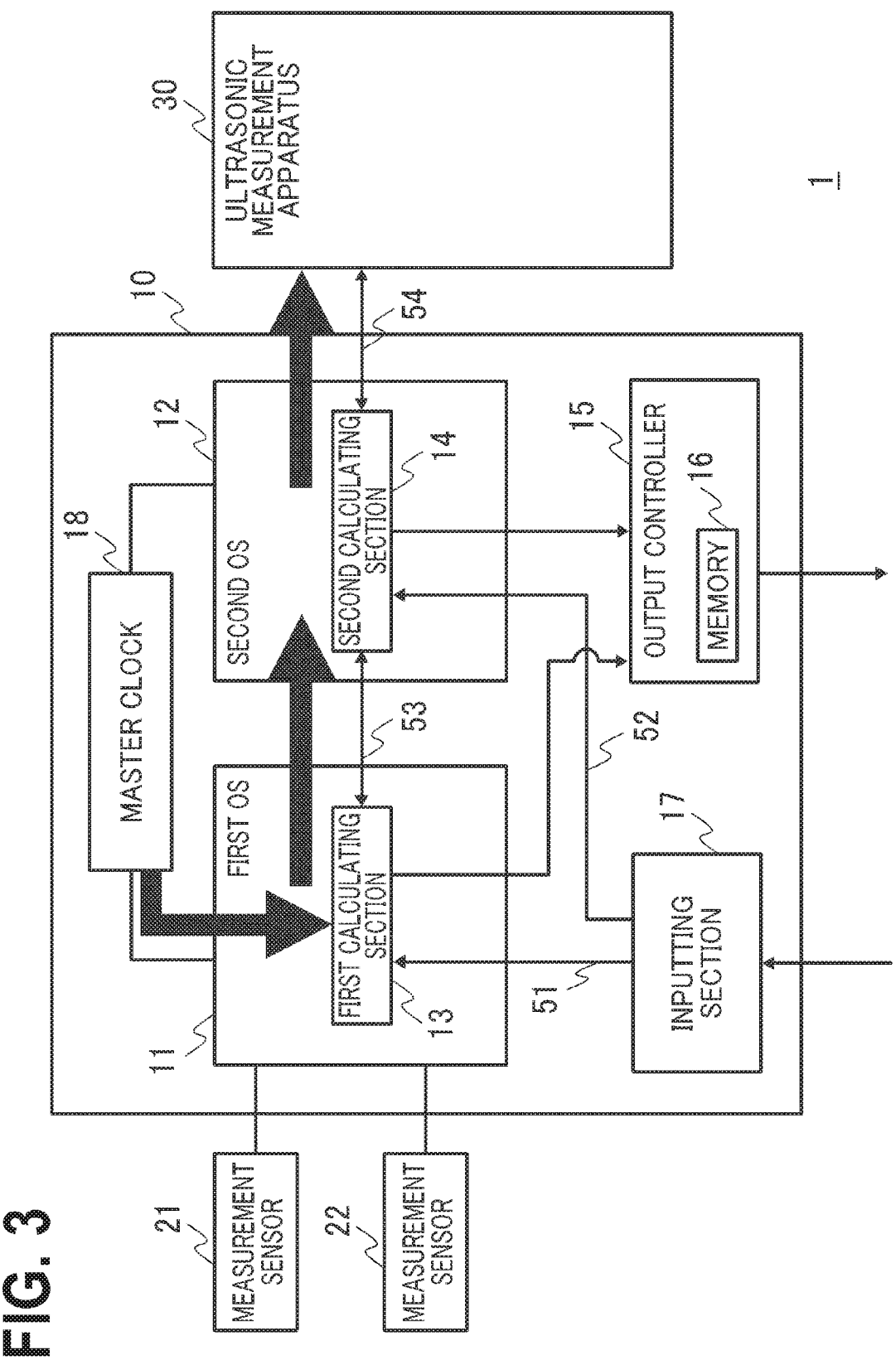
FIG. 3 is a block diagram illustrating the configuration of a patient monitor system 1 of Embodiment 2.

In the patient monitor system 1, the configuration itself is identical with that illustrated in FIG. 1. In the embodiment, the method of synchronizing the times when a predetermined event occurs is different. FIG. 3 illustrates the flow of the time synchronization in the embodiment.

When a predetermined event occurs, the first OS 11 reads the common time information from the master clock 18. The first OS 11 updates the first time information which is managed by oneself, by using the read-out common time information. Moreover, the first OS 11 notifies the second OS 12 of the updated first time information through the bus line 53. Alternatively, the first OS 11 may notify the second OS 12 of the common time information before the first time information is updated. Namely, the first OS 11 notifies the second OS 12 of the common time information or the updated first time information. The second OS 12 updates the second time information which is managed by oneself, by using the informed first time information or common time information. Moreover, the second OS 12 notifies the ultrasonic measurement apparatus 30 of the updated second time information. Alternatively, the second OS 12 may notify the ultrasonic measurement apparatus 30 of the common time information before the second time information is updated. Namely, the second OS 12 notifies the ultrasonic measurement apparatus 30 of the common time information or the updated second time information. The ultrasonic measurement apparatus 30 updates the time information which is managed by the own operating system, by using the informed second time information (or the common time information).

Then, the effect of the patient monitor 10 of the embodiment will be described. In the configuration of the embodiment, when a predetermined event occurs, similarly with Embodiment 1, the operating systems (the first OS 11, the second OS 12, and the operating system in the ultrasonic measurement apparatus 30) cause the sets of time information which are managed respectively by the OSs, to be synchronized with one another by using the common time information that is counted by the master clock 18. Consequently, the patient monitor 10 can handle a plurality of sets of information (a waveform, a measurement value, and an ultrasonic image) in a state where there is no time difference.

Embodiment 3

Then, a patient monitor system 1 of the embodiment 3 will be described. Hereinafter, the patient monitor system 1 of the embodiment 3 will be described in points different from Embodiment 1.

Figure 4:
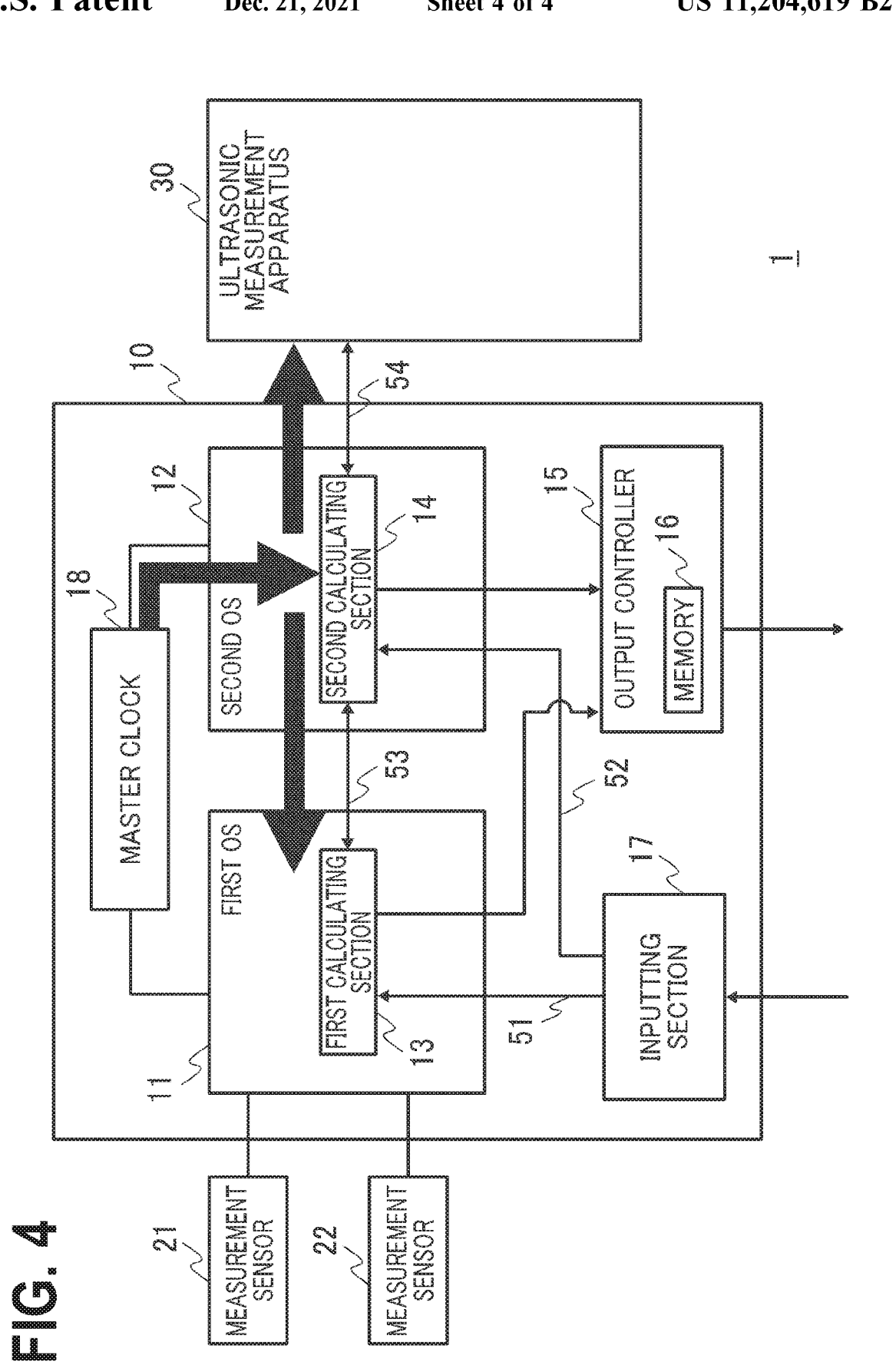
FIG. 4 is a block diagram illustrating the configuration of a patient monitor system 1 of Embodiment 3.

In the patient monitor system 1, the configuration itself is identical with that illustrated in FIG. 1. In the embodiment, the method of synchronizing the times when a predetermined event occurs is different. FIG. 4 illustrates the flow of the time synchronization in the embodiment.

When a predetermined event occurs, the second OS 12 reads the common time information from the master clock 18. The second OS 12 updates the second time information which is managed by oneself, by using the read-out common time information. Moreover, the second OS 12 notifies the first OS 11 of the updated second time information through the bus line 53. The first OS 11 updates the first time information which is managed by oneself, by using the informed second time information. Moreover, the second OS 12 notifies the ultrasonic measurement apparatus 30 of the updated second time information. The ultrasonic measurement apparatus 30 updates the time information which is managed by the own operating system, by using the informed second time information.

Alternatively, the second OS 12 may notify the first OS 11 and the ultrasonic measurement apparatus 30 of the common time information before the second time information is updated. Namely, the second OS 12 is requested to notify the first OS 11 and the ultrasonic measurement apparatus 30 of the common time information or the updated second time information.

Also the above-described configuration can attain an effect similar to the effects of Embodiments 1 and 2.

Although the invention conducted by the inventor has been specifically described based on the embodiments, the invention is not limited to the above-described embodiments, and it is a matter of course that various changes can be made without departing from the spirit of the invention.

For example, the first OS 11 or the second OS 12 may read time information from an NTP server (Network Time Protocol server, a time server) on a network at an arbitrary timing, and update the common time information which is managed by the master clock 18, by using the read-out time information. According to the configuration, the common time information which is managed by the master clock 18 is made substantially identical with a correct time on the network, and a state is obtained where also the sets of time information (the first time information, the second time information, the system clock of the ultrasonic measurement apparatus 30) which are managed respectively by the operating systems (the first OS 11, the second OS 12, and the operating system operating in the ultrasonic measurement apparatus 30) are synchronized with time information which is managed on the network.

In place of the ultrasonic measurement apparatus 30, an electromyograph, an EIT (Electrical Impedance Tomography) measurement apparatus, an electromagnetic blood flow meter, or the like may be used as the external measurement apparatus.

Moreover, the first OS 11 may store as a history the degree of the difference which, when the first time information is to be updated, is produced between the first time information and the common time information. Similarly, the second OS 12 may store as a history the degree of the difference which, when the second time information is to be updated, is produced between the second time information and the common time information. The operating systems may use the differences in the displayed vital signs or the like. For example, a case where, in the updating, a difference of 3 seconds exists at 10 minutes past 10 o'clock will be considered. In this case, when the history of the vital sign at 10 minutes past 10 o'clock is displayed, the first OS 11 (or the second OS 12) may cause the existence of the difference of 3 seconds to be displayed together with the display of the vital sign. The first OS 11 (or the second OS 12) may correct the history of the vital sign in accordance with the time difference. In the case where a difference of 3 seconds is caused in the time, for example, correction such as that in which the time information of the history of the vital sign immediately before the updating is shifted by 3 seconds may be performed.

The present application is based on Japanese Patent Application No. 2016-008260, filed on Jan. 19, 2016, the entire contents of which are incorporated herein by reference.

INDUSTRIAL APPLICABILITY

There is provided a patient monitor on which a plurality of operating systems operate, and in which, in a configuration where an external measurement apparatus is connected to the patient monitor, the operating systems can respectively handle time information without time difference.

REFERENCE SIGNS LIST

10 patient monitor,
11 first OS (operating system),
12 second OS (operating system),
13 first calculating section,
14 second calculating section,
15 output controller,
16 memory,
17 inputting section,
18 master clock,
21 measurement sensor,
22 measurement sensor,
30 ultrasonic measurement apparatus

The invention claimed is:

1. A patient monitor that acquires a vital sign of a subject through a measurement sensor, and that is to be connected to an external measurement apparatus for measuring another vital sign of the subject, the patient monitor comprising:
   a master clock that is disposed in the patient monitor, and that manages common time information that is time information common to hardware;
   a first operating system that manages first time information that is internal specific time information and measures the vital sign of the subject; and
   a second operating system that manages second time information that is internal specific time information, and that transmits and receives data to and from the external measurement apparatus,
   wherein, when a predetermined event that relates to measurement of the another vital sign by the external measurement apparatus occurs, the first operating system reads the common time information from the master clock, and updates the first time information by using the common time information, and when the predetermined event occurs, the second operating system reads the common time information from the master clock, updates the second time information by using the common time information, and notifies the external measurement apparatus of the updated second time information or the common time information.

2. The patient monitor according to claim 1 wherein the first operating system or the second operating system updates the common time information which is managed by the master clock, by using time information which is read from a time server on a network.

3. The patient monitor according to claim 1, wherein the first operating system executes a process of updating the first time information, in preference to other processes.

4. The patient monitor according to claim 1, wherein the second operating system executes a process of updating the second time information, in preference to other processes.

5. The patient monitor according to claim 1, wherein the patient monitor and the external measurement apparatus are connected to each other in a wired manner.

6. The patient monitor according to claim 1, wherein the first operating system is configured to execute a preset specific function, and the second operating system is a general-purpose operating system.

7. A patient monitor that acquires a vital sign of a subject through a measurement sensor, and that is to be connected to an external measurement apparatus for measuring another vital sign of the subject, the patient monitor comprising:
- a master clock that is disposed in the patient monitor, and that manages common time information that is time information common to hardware;
- a first operating system that manages first time information that is internal specific time information and measures the vital sign of the subject; and
- a second operating system that manages second time information that is internal specific time information, and that transmits and receives data to and from the external measurement apparatus,
- wherein, when a predetermined event that relates to measurement of the another vital sign by the external measurement apparatus occurs, the first operating system reads the common time information from the master clock, updates the first time information by using the common time information, and notifies the second operating system of the updated first time information or the common time information, and
- the second operating system updates the second time information by using the updated first time information or common time information which is notified from the first operating system, and notifies the external measurement apparatus of the updated second time information or the common time information.

8. The patient monitor according to claim 7, wherein the first operating system or the second operating system updates the common time information which is managed by the master clock, by using time information which is read from a time server on a network.

9. The patient monitor according to claim 7, wherein the first operating system executes a process of updating the first time information, in preference to other processes.

10. The patient monitor according to claim 7, wherein the second operating system executes a process of updating the second time information, in preference to other processes.

11. The patient monitor according to claim 7, wherein the patient monitor and the external measurement apparatus are connected to each other in a wired manner.

12. The patient monitor according to claim 7, wherein the first operating system is configured to execute a preset specific function, and the second operating system is a general-purpose operating system.

13. A patient monitor that acquires a vital sign of a subject through a measurement sensor, and that is to be connected to an external measurement apparatus for measuring another vital sign of the subject, the patient monitor comprising:
- a master clock that is disposed in the patient monitor, and that manages common time information that is time information common to hardware;
- a first operating system that manages first time information that is internal specific time information and measures the vital sign of the subject; and
- a second operating system that manages second time information that is internal specific time information, and that transmits and receives data to and from the external measurement apparatus,
- wherein, when a predetermined event that relates to measurement of the another vital sign by the external measurement apparatus occurs, the second operating system reads the common time information from the master clock, updates the second time information by using the common time information, and notifies the first operating system and the external measurement apparatus of the common time information or the updated second time information, and
- the first operating system updates the first time information by using the common time information or second time information which is notified from the second operating system.

14. The patient monitor according to claim 13, wherein the first operating system or the second operating system updates the common time information which is managed by the master clock, by using time information which is read from a time server on a network.

15. The patient monitor according to claim 13, wherein the first operating system executes a process of updating the first time information, in preference to other processes.

16. The patient monitor according to claim 13, wherein the second operating system executes a process of updating the second time information, in preference to other processes.

17. The patient monitor according to claim 13, wherein the patient monitor and the external measurement apparatus are connected to each other in a wired manner.

18. The patient monitor according to claim 13, wherein the first operating system is configured to execute a preset specific function, and the second operating system is a general-purpose operating system.

* * * * *